(12) United States Patent
Weber et al.

(10) Patent No.: US 8,367,699 B2
(45) Date of Patent: Feb. 5, 2013

(54) TETRAHYDRO-ISOQUINOLINES

(75) Inventors: Lutz Weber, Germering (DE); Vladimir Khazak, Brooklyn, NY (US); Gunther Ross, Munich (DE); Cedric Kalinski, Munich (DE); Christoph Burdack, Munich (DE)

(73) Assignee: NexusPharma, Inc., Langhorne, PA (US)

( * ) Notice: Subject to any disclaimer, the term of this patent is extended or adjusted under 35 U.S.C. 154(b) by 637 days.

(21) Appl. No.: 12/441,266

(22) PCT Filed: Sep. 14, 2007

(86) PCT No.: PCT/US2007/078464
§ 371 (c)(1),
(2), (4) Date: Aug. 18, 2009

(87) PCT Pub. No.: WO2008/034039
PCT Pub. Date: Mar. 20, 2008

(65) Prior Publication Data
US 2009/0306130 A1    Dec. 10, 2009

Related U.S. Application Data

(60) Provisional application No. 60/845,095, filed on Sep. 15, 2006.

(51) Int. Cl.
C07D 217/02 (2006.01)
A61K 31/47 (2006.01)

(52) U.S. Cl. .................... 514/307; 546/146
(58) Field of Classification Search ............ None
See application file for complete search history.

(56) References Cited

U.S. PATENT DOCUMENTS 6,664,269 B2   12/2003   Martin et al.
8,163,744 B2    4/2012   Weber et al.

OTHER PUBLICATIONS

West, Anthony R., Solid State Chemistry and its Applications, Wiley, New York, 1988, pp. 358 & 365.*
Wu, Toxicology, vol. 236, 2007, pp. 1-6.*
Gitto, Arkivoc, 2004, vol. (v), p. 170-180.*
Stoyanova et al, Journal of Heterocyclic Chemistry (2003), 40(5), 795-803.*
Chemical Abstract 94:64698,Terent'ev et al, Khimiya Geterotsiklicheskikh Soedinenii (1980), (10), 1395-7.*
English language translation of Terent'ev et al, Khimiya Geterotsiklicheskikh Soedinenii (1980), (10), 1395-7.*
Garcia-Echeverria, Carlos et al., "Discovery of Potent Antagonists of the Interaction between Human Double Minute 2 and Tumor Suppressor p53", J. Med. Chem., 43: 3205-3208 (2000).
Bres, Vanessa et al., "A non-proteolytic role for ubiquitin in Tat-mediated transaction of the HIV-1 promoter", Nature Cell Biology, 5(8): 754-761 (2003).

Fisher, Matthew J. et al., "Non-Peptide RGD Surrogates Which Mimic a Gly-Asp B-Turn: Potent Antagonists of Platelet Glycoprotein IIb-IIIa", J. Med. Chem., 40: 2085-2101 (1997).
Galatin, Peter S. et al., "A Nonpeptidic Sulfonamide Inhibits the p53-=mdm2 Interaction and Activates p53-Dependent Transcription in mdm2-Overexpressing Cells", J. Med. Chem., 47: 4163-4165 (2004).
Grasberger, Bruce L. et al., "Discovery and Cocrystal Structure of Benzodiazepinedione HDM2 Antagonists That Activate p53 in Cells", J. Med. Chem., 48: 909-912 (2005).
Hardcastle, Ian R. et al., "Isoindolinone-based inhibitors of the MDM2-p53 protein-protein interaction", Bioorganic & Medicinal Chemistry Letters, 15: 1515-1520 (2005).
Henning, Wilhelm et al., "MDM2 is a Target of Simian Virus 40 in Cellular Transformation and during Lytic Infection", Journal of Virology, 71(10): 7609-7618 (1997).
Hollstein, Monica et al., "p53 Mutations in Human Cancers", Science, 253: 49-53 (1991).
Juven-Gershon, Tamar et al., "The Mdm2 Oncoprotein Interacts with the Cell Fate Regulator Numb", Molecular and Cellular Biology, 18(7): 3974-3982 (1998).
Machida, Keigo et al., "Hepatitis C virus induces a mutator phenotype: Enhanced mutations of immunoglobulin and protooncogenes", PNAS, 101(12): 4262-4267 (2004).
Michael, Dan et al., "The p53-Mdm2 module and the ubiquitin system", Seminars in Cancer Biology, 13: 49-58 (2003).
Momand, Jamil et al., "The MDM2 gene amplification database", Nucleic Acids Research, 26(15): 3453-3459 (1998).
O'Shea, Clodugh C. et al., "Modulation of the ARF-p53 Pathway by the Small DNA Tumor Viruses", Cell Cycle, 4: 449-452 (2005).
Parks, Daniel J. et al., "1,4-Benzodiazepine-2,5-diones as small molecule antagonists of the HDM2-p53 interaction: discovery and SAR", Bioorganic & Medicinal Chemistry Letters, 15: 765-770 (2005).

(Continued)

Primary Examiner — Zinna Northington Davis
(74) Attorney, Agent, or Firm — Patrick J. Hagan; Dann, Dorfman, Herrell and Skillman, PC

(57) ABSTRACT

The present invention provides a compound selected from compounds of formula (A) as ligand binding to the HDM2 protein, inducing apoptosis and inhibiting proliferation, and having therapeutic utility in cancer therapy and prevention. Compounds of formula (A) can be used as therapeutics for treating stroke, myocardial infarction, ischemia, multi-organ failure, spinal cord injury, Alzheimer's Disease, injury from ischemic events and heart valvular degenerative disease. Moreover, compounds of formula (A) can be used to decrease the side effects from cytotoxic cancer agents, radiation and to treat viral infections.

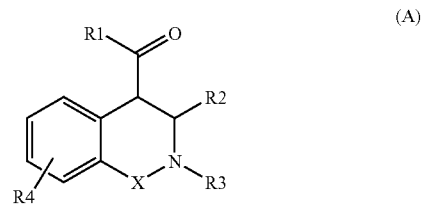

14 Claims, No Drawings

OTHER PUBLICATIONS

Vassilev, Lyubomir T. et al., "In Vivo Activation of the p53 Pathway by Small-Molecule Antagonists of MDM2", Science (2003).

Vousden, Karen H. et al., "Live or Let Die: the Cell's Response to p53", Nature, 2: 594-604 (2002).

Wang, Limin et al., "One-Pot Synthesis of cis-Isoquinolonic Acid Derivatives via Three-Component Reaction of Homophthalic Anhydride with Aldehydes and Amines using Ytterbium (iii) Triflate as Catalyst", Adv. Synth. Catal., 347: 689-694 (2005).

Yadav, J.S. et al., "Room temperature ionic liquids promoted three-component coupling reactions: a facile synthesis of cis-isoquinolonic acids", Tetrahedron, 59: 1805-1809 (2003).

Yang, Hai Liang et al., "Adenovirus-mediated E2F-1 Gene Transfer Inhibits MDM2 Expression and Efficiently Induces Apoptosis in MDM2-overexpressing Tumor Cells", Clinical Cancer Research, 5: 2242-2250 (1999).

Zhang, Zhuo et al., "MDM2 is a Negative Regulator of p21 WAF1/CIP1, Independent of p53", J. Biol. Chem., 279(16): 16000-16006 (2004).

Zhang, Zhuo et al., "Antisense therapy targeting MDM2 oncogene in prostate cancer: Effects on proliferation, apoptosis, multiple gene expression, and chemotherapy", PNAS, 100(20): 11636-11641 (2003).

Zhao, Jianhua et al., "The initial evaluation of non-peptidic small-molecule HDM2 inhibitors based on p53-HDM2 complex structure", Cancer Letters, 183: 69-77 (2002).

Moule, Madeleine G. et al., "Role for PP2A in ARF signaling to p53", PNAS, 101(39) 14063-14066 (2004).

Kandinska, Meglena I. et al., "Synthesis of New trans-2-Benzyl-3-(furan-2-yl)-4-substituted-1,2,3,4-tetrahydroisoquinolines", Molecules,11: 403-414 (2006).

Stoyanova, Malinka P. et al., "Synthesis of trans1 cis 4-substituted 3-furyl-2-phenethyltetrahydroisoquinolin-1-ones: conformation of the trans-4-(pyrrolidinylcarbonyl) derivative", Tetrahedron Letters, 47: 2119-2123 (2006).

* cited by examiner

TETRAHYDRO-ISOQUINOLINES

CROSS-REFERENCE TO RELATED APPLICATIONS

This application is the U.S. National Stage of International Application No. PCT/US2007/078464, filed Sep. 14, 2007, which claims priority from U.S. Provisional Application No. 60/845,095, filed Sep. 15, 2006. The entire disclosure of each the aforesaid applications is incorporated by reference in the present application.

BACKGROUND OF THE INVENTION

HDM2 plays a central role in regulating and influencing important cell-signaling pathways. HDM2 is known to interact with a range of different proteins that influence cellular apoptosis, proliferation and survival.

Thus, amongst other proteins, HDM2 binds to the tumor suppressor protein p53 and targets this protein for ubiquitination and degradation, prevents translocation of p53 to the nucleus by facilitating translocation to the microsomes. Thereby, HDM2 prevents transactivation of p53 target genes that are implicated in the regulation of cell cycle and apoptosis. The p53 protein is a potent cell cycle inhibitor that prevents propagation of permanently damaged cell clones by the induction of growth arrest or apoptosis, resulting in the protection against development of cancer by guarding cellular integrity.

Both p53 as well as HDM2 can be associated with cancer: about 50% of all human tumors harbor a mutation or deletion in the p53 gene that impairs normal p53 function (Hollstein et al. *Science* 1991, 253, 49-53). In many cancers with wild-type p53, HDM2 is overexpressed, disabling the normal p53 function (Momand et al. *Nucleic Acids Res.* 1998, 26, 3453-3459).

The HDM2 gene has a p53-responsive promoter element and elevated levels of p53 that translocate to the nucleus induce expression of HDM2. Induction of HDM2 by p53 forms an autoregulatory feedback loop, ensuring low levels of both HDM2 and p53 in normally proliferating cells (Michael and Oren *Semin. Cancer Biol.* 2003, 13, 49-58; Vousden and Lu *Nature Reviews Cancer* 2002, 2, 594-604). However, in many cancers this normal ratio of HDM2 to p53 is changed and misregulated.

Inhibiting the interaction of HDM2 with p53 in cells with wild-type p53 or mutated p53 should lead to an increase of p53 levels in the cytosole, facilitating normal nuclear translocation of normal or mutated p53, cell cycle arrest and/or apoptosis and restoring the tumor suppressor role of p53. The feasibility of this strategy has been shown by the use of different macromolecular tools for inhibition of HDM2-p53 interaction (e.g. antibodies, antisense oligonucleotides, peptides).

HDM2 also binds to the tumour suppressor pRB, as well as E2F-1 (Yang et al. *Clinical Cancer Research* 1999, 5, 2242-2250).

E2F-1 is a transcription factor that regulates S phase entry and has been shown to cause apoptosis in some cell types when overexpressed. HDM2 binds to E2F through a conserved binding region at p53, activating E2F-dependent transcription of cyclin A, and suggesting that HDM2 small molecule ligands or antagonists might have also anti-tumor effects in cells independent of their role of restoring p53 function.

HDM2 can associate in vitro and in vivo with the mammalian Numb protein. The association occurs through the N-terminal domain of HDM2, which is the region also involved in p53 binding. The Numb protein is involved in the regulation of cell fate and in a variety of developmental processes, most notably in the nervous system. Through its interaction with Numb, HDM2 may influence processes such as differentiation and survival. This could also contribute to the altered properties of tumour cells, which overexpress HDM2 (Juven-Gershon et al. *Mol. Cell. Biol.* 1998, 18, 3974-3982).

There is also evidence that HDM2 has a direct role in the regulation of p21, a cyclin-dependent kinase inhibitor. The inhibition of HDM2 with anti-HDM2 antisense oligonucleotide or Short Interference RNA targeting HDM2 significantly elevates p21 protein levels in p53 null PC3 cells. In contrast, overexpression of HDM2 diminishes p21 levels by shortening the p21 half-life, an effect reversed by HDM2 antisense inhibition. HDM2 facilitates p21 degradation independent of ubiquitination and the E3 ligase function of HDM2. Instead, HDM2 promotes p21 degradation by facilitating binding of p21 with the proteasomal C8 subunit. The p21 and HDM2 bind through 180—the 298 amino acids region of the HDM2 protein (Zhang et al. *J. Biol. Chem.* 2004, 279, 16000-16006).

There is also evidence for a malfunctioning HDM2 regulation having effect on a proper p53 function and causing cancer, beyond mutated p53 or overexpression of HDM2. Thus, when E2F signals the growth of a cancer, P14ARF is dispatched to break down HDM2, freeing p53 to kill the cancer cell. In certain cancers P14ARF is lacking (Moule et al. *Proc. Natl. Acad. Sci. U.S.A.* 2004, 101, 14063-6). P14ARF binds to HDM2 and promotes the rapid degradation of HDM2. ARF-mediated HDM2 degradation is associated with HDM2 modification and concurrent p53 stabilization and accumulation.

The validity of inhibiting HDM2 as a therapeutic concept has been first demonstrated by antisense HDM2 inhibitors that exhibit significant antitumor activity in multiple human cancer models with various p53 statuses (Zhang et al. *Proc. Natl. Acad. Sci. U.S.A.* 2003, 100, 11636-11641).

Small molecule antagonists of the HDM2 protein interactions may therefore offer a viable approach towards cancer therapy, either as single agents or in combination with a broad variety of other anti-tumour therapies.

There is also growing evidence that HDM2 plays an important role in viral infections. First, it is known that viruses rely on changing normal p53 signaling (O'shea and Fried M. *Cell Cycle* 2005; Machida et al. *Proc. Natl. Acad. Sci. U.S.A.* 2004, 23, 101, 4262-7). Second, HDM2 directly interacts with viral proteins, for example HDM2 is a target of simian virus 40 in cellular transformation and during lytic infection (Henning et al. *J. Virol.* 1997, 71, 7609-7618). Furthermore, the HDM2 protein, like p53, becomes metabolically stabilized in SV40-transformed cells. This suggests the possibility that the specific targeting of HDM2 by SV40 is aimed at preventing HDM2-directed proteasomal degradation of p53 in SV40-infected and -transformed cells, thereby leading to metabolic stabilization of p53 in these cells. A trimeric LT-p53-HDM2 complex is formed with simian virus 40 large tumour antigen (LT) in SV40-transformed cells. The human immunodeficiency virus type 1 (HIV-1) encodes a potent transactivator, Tat. HDM2 has been shown to interact with Tat and mediating its ubiquitination in vitro and in vivo. In addition, HDM2 is a positive regulator of Tat-mediated transactivation, indicating that the transcriptional properties of Tat are stimulated by ubiquitination (Bres et al. *Nat Cell Biol.* 2003, 5, 754-61).

Small molecule inhibitors of the HDM2 interaction have been reported and show pro-apoptotic effects in in vitro models and an antitumour effect in animal models of cancer. Thus, benzodiazepines have been used as a chemical scaffold to achieve HDM2 inhibitory activity (Grasberger et al. *J. Med. Chem.* 2005, 48, 909-912; Parks et al. *Bioorganic & Medicinal Chemistry Letters* 2005, 15, 765-770). Similarly, imidazolines (Vassilev et al. *Science* 2004, 303, 844-848), isoindolones (Hardcastle et al. *Bioorganic & Medicinal Chemistry Letters* 2005, 15, 1515-1520), norbornanes (Zhao et al. *Cancer Letters* 2002, 183, 69-77) and sulfonamides (Galatin and Abraham *J. Med. Chem.* 2004, 47, 4163-4165) have been reported as small molecule HDM2 inhibitors.

It has also been reported that HDM2 ligands have a cytoprotective effect. Thus, HDM2 inhibitors can be employed in methods of inducing cytoprotection and are useful to protect non-target cells against the harmful effects of chemotherapeutic agents. The amount of HDM2 inhibitor that provides such an effect can be about 5 to about 10 fold lower than the amount needed to induce apoptosis (Koblish et al. WO03095625, METHOD FOR CYTOPROTECTION THROUGH HDM2 AND HDM2 INHIBITION, 2003-11-20).

Isoquinolones have been reported already as potent antagonists of the platelet glycoprotein IIb-IIIa (Fisher et al. *J. Med. Chem.* 1997, 40, 2085-2101) to treat cardiovascular diseases. Pancrastatin is a naturally occurring alkaloid with an isoquinolone structure exhibiting anticancer properties, by acting on the tubulin cytosceleton. Lysolipin and Cervinomycin are antibiotics isolated from streptomyces violaceoniger. Lycoricidine and narciclasine are isoquinolone based plant-growth regulators, Gliquidone is an antidiabetic medication which is used in those patients with adult maturity onset or non-insulin dependent diabetes (NIDDM). It works by lowering blood sugar levels by stimulating the production and release of insulin from the pancreas. It also promotes the movement of sugar from the blood into the cells in the body which need it. Tesicam is an isoquinolon-dione used for its anti-inflammatory properties. These compounds have low toxicity, good pharmaco-kinetic properties and render the chemical class of isoquinolones an interesting scaffold for new drug candidates.

In the present invention, we describe novel small molecules, which are based on a isoquinolone scaffold, which bind to HDM2, are inhibitors of HDM2 mediated biology and can be used as novel therapeutic agents.

SUMMARY OF THE INVENTION

The present invention provides compounds of formula (A) and the pharmaceutically acceptable salts and esters thereof, which are ligands binding to the HDM2 protein, inducing apoptosis and inhibiting proliferation, and having therapeutic utility in cancer therapy and prevention. This therapeutic effect can be achieved by using compounds of formula (A) alone or in combination with other agents that are used to treat or prevent cancer.

Second, compounds of formula (A) also can be used to treat or prevent cancer by protecting non-cancer cells from the deleterious effects of cancer treating drugs. In this treatment, a combination of an antineoplastic agent and a cytoprotective amount of at least one compound of formula (A), and one or more pharmaceutically acceptable excipients are used. The compound of formula (A), also called HDM2 ligand is administered prior to, concurrently or after administration of the antineoplastic agent. Additionally, the HDM2 inhibitor can be administered continuously or at repeated regular intervals.

Third, a compound selected from compounds of formula (A) can be used as a therapeutic agent in methods of treating stroke, myocardial infarction, ischemia, multi-organ failure, spinal cord injury, Alzheimer's Disease, injury from ischemic events, heart valvular degenerative disease or decreasing the side effects from cytotoxic agents, such as hair loss or cardio toxicity induced by doxorubicin or paclitaxel.

Fourth, a compound selected from compounds of formula (A) of the present invention can be used to treat viral infections, especially in a pharmaceutical combination comprising a known antiviral compound.

Fifth, a compound of formula (A) of the present invention is directed to a pharmaceutical composition comprising a cytoprotective amount of an HDM2 ligand, and one or more pharmaceutically acceptable excipients.

DETAILED DESCRIPTION OF THE INVENTION

The present invention provides novel isoquinoline derivatives that are small molecule ligands of the HDM2 protein and prevent binding of other proteins to HDM2.

In in vitro cell-based assays, compounds of the present invention inhibit the interaction of the HDM2 protein with the p53 protein. In such cell-based assays, these compounds demonstrate mechanistic activity such as induction of apoptosis and inhibition of proliferation. Incubation of cancer cells with compounds of formula (A) leads to an accumulation of p53 protein, induction of p53-regulated p21 gene, and cell cycle arrest in G1 and G2 phase, resulting in potent antiproliferative activity against wild-type p53 cells in vitro. In contrast, these activities were not observed in cancer cells with missing p53 at comparable compound concentrations. Therefore, the activity of HDM2 antagonists is likely linked to its mechanism of action. These compounds can be potent and selective anticancer agents.

The present invention provides a compound of general formula (A) and the pharmaceutically acceptable esters and salts thereof,

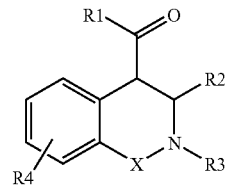

formula (A)

wherein
X is C=O,
R1 is selected from substituted or unsubstituted morpholinyl, substituted or unsubstituted pyrrolidinyl and substituted or unsubstituted piperazinyl, —O(X1) or —NX1(X2), with X1 and X2 independently selected from H, alkyl, cycloalkyl, heteroalkyl, aryl, heteroaryl, arylalkyl or heteroarylalkyl,
wherein R2 is selected from heteroaryl,
wherein R3 is selected from aryl, heteroaryl, arylalkyl or heteroarylalkyl,
wherein R4 is selected from —H, —F, —Cl, —Br, —I, —NO2, hydroxy, lower alkyl, lower alkenyl or lower alkinyl, lower alkoxy, such as —OCH$_3$, —CH$_2$OCH$_3$ and —CH$_2$OCH$_2$CH$_3$, —NY1(Y2), with Y1 and Y2 independently selected from H, lower alkyl, lower alkoxy alkyl, hetero alkyl, aryl or heteroaryl.

The present invention especially provides a compound of formula (I) and the pharmaceutically acceptable esters and salts thereof,

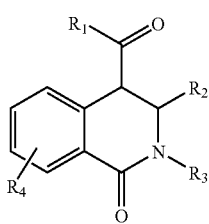

formula (I)

wherein
R1 is selected from substituted or unsubstituted morpholinyl, substituted or unsubstituted pyrrolidinyl and substituted or unsubstituted piperazinyl, —O(X1) or —NX1(X2), with X1 and X2 independently selected from H, alkyl, cycloalkyl, heteroalkyl, aryl, heteroaryl, arylalkyl or heteroarylalkyl,
wherein R2 is selected from heteroaryl,
wherein R3 is selected from aryl, heteroaryl, arylalkyl or heteroarylalkyl,
wherein R4 is selected from —H, —F, —Cl, —Br, —I, —NO2, hydroxy, lower alkyl, lower alkenyl or lower alkinyl, lower alkoxy, such as —OCH$_3$, —CH$_2$OCH$_3$ and —CH$_2$OCH$_2$CH$_3$, —NY1(Y1), with Y1 and Y2 independently selected from H, lower alkyl, lower alkoxy alkyl, hetero alkyl, aryl or heteroaryl.

In the context of this invention, the term alkyl denotes a saturated or unsaturated (i.e. alkenyl and alkinyl) straight or branched chain hydrocarbon group, containing preferably from one to ten, more preferably one to six carbon atoms, for example a methyl, ethyl, propyl, iso-propyl, butyl, iso-butyl, sec-butyl, tert-butyl, n-pentyl, iso-pentyl n-hexyl, 2,2-dimethylbutyl, n-octyl; ethenyl (vinyl), propenyl (allyl), iso-propenyl, n-pentyl, butenyl, isoprenyl or hexa-2-enyl; ethinyl, propinyl or butinyl groups. Any alkyl group as defined herein may be substituted with one, two or more atoms or atom groups as substituents, for example a F, Cl, Br, or I atom, or a NH$_2$, OH, SH, COOH or NO$_2$ group, wherein one or more, preferably one or two, of the hydrogen atoms of the alkyl residue are independently of each other replaced by one or more of the above defined substituents.

The terms alkenyl and alkinyl denotes an unsaturated straight or branched chain alkyl group (having one, two or more double and/or triple bonds, an alkenyl preferably having one or two double bonds and an alkinyl preferably having one or two triple bonds), containing from two to ten, preferably two to six carbon atoms for example: ethenyl (vinyl), propenyl (allyl), isopropenyl, n-pentenyl, butenyl, isoprenyl or hexa-2-enyl; ethinyl, propinyl or butinyl groups. Any alkenyl or alkinyl group as defined herein may be substituted with one, two or more substituents, for example F, Cl, Br, I, NH$_2$, OH, SH, COOH or NO$_2$, wherein one or more, preferably one or two, of the hydrogen atoms of the respective residue are independently of each other replaced by one or more of the above defined substituents.

The term heteroalkyl denotes an alkyl group as defined herein wherein one or more carbon atoms, preferably one, two or three carbon atoms, are independently of each other replaced by an oxygen, nitrogen, phosphorous or sulphur atom, for example an alkoxy group such as methoxy, ethoxy, propoxy, iso-propoxy, butoxy or tert-butoxy, an alkoxyalkyl group such as methoxymethyl, ethoxymethyl, 1-methoxyethyl, 1-ethoxyethyl, 2-methoxyethyl or 2-ethoxyethyl, an alkylamino group such as methylamino, ethylamino, propylamino, isopropylamino, dimethylamino or diethylamino, an alkylthio group such as methylthio, ethylthio or isopropylthio or a cyano group. It may also refer to one of the above groups containing a keto group. The term heteroalkyl furthermore refers to a group derived from a carboxylic acid or carboxylic acid amide such as acetyl, propionyl, acetyloxy, propionyloxy, acetylamino or propionylamino, a carboxyalkyl group such as carboxymethyl, carboxyethyl or carboxypropyl, a carboxyalkyl ester, an alkylthiocarboxyamino group, an alkoxyimino group, an alkylaminothiocarboxyamino group or an alkoxycarbonylamino group. Any heteroalkyl group as defined herein may be substituted with one, two or more substituents, for example F, Cl, Br, I, NH$_2$, OH, SH, COOH or NO$_2$, wherein one or more, preferably one or two, of the hydrogen atoms of the heteroalkyl residue are independently of each other replaced by one or more of the above defined substituents.

Examples of heteroalkyl groups are groups of formulae $R^a$—O—$Y^a$—, $R^a$—S—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, $R^a$ being a hydrogen atom, a $C_1$-$C_6$alkyl, a $C_2$-$C_6$alkenyl or a $C_2$-$C_6$alkynyl group; $R^b$ being a hydrogen atom, a $C_1$-$C_6$alkyl, a $C_2$-$C_6$alkenyl or a $C_2$-$C_6$alkynyl group; $R^c$ being a hydrogen atom, a $C_1$-$C_6$alkyl, a $C_2$-$C_6$alkenyl or a $C_2$-$C_6$alkynyl group; $R^d$ being a hydrogen atom, a $C_1$-$C_6$alkyl, a $C_2$-$C_6$alkenyl or a $C_2$-$C_6$alkynyl group and $Y^a$ being a bond, a $C_1$-$C_6$alkylene, a $C_2$-$C_6$alkenylene or a $C_2$-$C_6$alkynylene group, each heteroalkyl group containing at least one carbon atom and it being possible for one or more hydrogen atoms to have been replaced by fluorine or chlorine atoms. Specific examples of heteroalkyl groups are methoxy, trifluoromethoxy, ethoxy, n-propyloxy, isopropyloxy, tert-butyloxy, methoxymethyl, ethoxymethyl, methoxyethyl, methylamino, ethylamino, dimethylamino, diethylamino, isopropylethylamino, methylaminomethyl, ethylaminomethyl, diisopropylaminoethyl, enol ether, dimethylaminomethyl, dimethylaminoethyl, acetyl, propionyl, butyryloxy, acetyloxy, methoxycarbonyl, ethoxycarbonyl, N-ethyl-N-methylcarbamoyl and N-methylcarbamoyl. Further examples of heteroalkyl groups are nitrile, isonitrile, cyanate, thiocyanate, isocyanate, isothiocyanate and alkylnitrile groups. An example of a heteroalkylene group is a group of formula —CH$_2$CH(OH)— or —CONH—.

The term cycloalkyl refers to a saturated or partially unsaturated (for example having one, two or more double and/or triple bonds), cyclic group with one, two or more rings, having three to 14 carbon ring-atoms, preferably from five or six to ten carbon ring-atoms, for example cyclopropyl, cyclobutyl, cyclopentyl, cyclohexyl, tetralin, cyclopentenyl or cyclohex-2-enyl groups. Any cycloalkyl group as defined herein may be substituted with one, two or more substituents, for example F, Cl, Br, I, OH, NH$_2$, SH, N$_3$, NO$_2$, alkyl groups such as methyl or ethyl, heteroalkyl groups such as methoxy, methylamino, dimethylamino, cyanide, or a group of the formula —OR, wherein R is hydrogen, a group of formula $PO_3R'R''$ or $SO_3R'$ or a heteroalkyl group carrying at least one OH, NH2, $SO_3R'$, $PO_3R'R''$ or COOH group, wherein R' is H, alkyl, cycloalkyl, aryl, arylalkyl, and wherein R" is H, alkyl, cycloalkyl, aryl, arylalkyl.

The expression heterocycloalkyl refers to a cycloalkyl group as defined above in which one or more (preferably 1, 2 or 3) ring carbon atoms have been replaced each independently of the others by an oxygen, nitrogen, silicon, selenium, phosphorus or sulphur atom (preferably oxygen, sulphur or nitrogen). A heterocycloalkyl group has preferably 1 or 2 ring(s) containing from 3 to 10 (especially 3, 4, 5, 6 or 7) ring atoms. The expression heterocycloalkyl refers furthermore to groups in which one or more hydrogen atoms have been replaced each independently of the others by fluorine, chlorine, bromine or iodine atoms or by OH, $=$O, SH, $=$S, $NH_2$, $=$NH or $NO_2$ groups. Examples are a piperidyl, piperazinyl, morpholinyl, urotropinyl, pyrrolidinyl, tetrahydrothiophenyl, tetrahydropyranyl, tetrahydrofuryl or 2-pyrazolinyl group and also lactams, lactones, cyclic imides and cyclic anhydrides.

The term aryl refers to an aromatic cyclic group with one, two or more rings, having five to 14 carbon ring-atoms preferably from five or six to ten carbon ring-atoms, for example phenyl or naphthyl groups. Any aryl group as defined herein may be substituted with one, two or more substituents, for example F, Cl, Br, I, OH, $NH_2$, SH, $N_3$, $NO_2$, alkyl groups such as methyl or ethyl, heteroalkyl groups such as methoxy, methylamino, dimethylamino or cyanide, wherein one or more, preferably one or two, of the hydrogen atoms of the aryl residue are independently of each other replaced by one or more of the above defined substituents. Examples are a phenyl, naphthyl, biphenyl, 2-fluorophenyl, anilinyl, 3-nitrophenyl or 4-hydroxyphenyl group.

The term heteroaryl refers to an aryl group as defined herein wherein one, two or more, preferably one or two, ring-carbon atoms are independently of each other replaced by an oxygen, nitrogen, boron, phosphorous or sulphur atom, for example a pyridyl, imidazolyl, pyrazolyl, quinolinyl, indolyl, benzimidazolyl, benzoxazolyl, benzisoxazolyl, benzthiazolyl, isoquinolinyl, pyrrolyl, oxazolyl, isoxazolyl, thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl and pyridazinyl groups. Any heteroaryl group as defined herein may be substituted with one, two or more substituents, for example F, Cl, Br, I, OH, $NH_2$, SH, $N_3$, $NO_2$, alkyl groups such as methyl or ethyl, heteroalkyl groups such as methoxy, methylamino, dimethylamino or cyanide, wherein one or more, preferably one or two, of the hydrogen atoms of the heteroaryl residue are independently of each other replaced by one or more of the above defined substituents.

The terms arylalkyl and heteroarylalkyl refer to groups that comprise both aryl or, respectively, heteroaryl as well as alkyl and/or heteroalkyl and/or cycloalkyl groups.

The expression arylalkyl (or aralkyl) refers to groups containing both aryl and also alkyl, alkenyl, alkynyl and/or cycloalkyl groups in accordance with the above definitions, such as, for example, arylalkyl, arylalkenyl, arylalkynyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1H-indene, tetralin, dihydronaphthalene, indanone, phenylcyclopentyl, cumene, cyclohexylphenyl, fluorene and indan. An aralkyl group preferably contains one or two aromatic ring systems (1 or 2 rings) containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroarylalkyl (or heteroaralkyl) refers to an arylalkyl (or aralkyl) group as defined above in which one or more (preferably 1, 2, 3 or 4) carbon atoms have been replaced each independently of the others by an oxygen, nitrogen, silicon, selenium, phosphorus, boron or sulphur atom (preferably oxygen, sulphur or nitrogen), that is to say to groups containing both aryl or heteroaryl and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (1 or 2 rings) containing from 5 or 6 to 10 ring carbon atoms and one or two alkyl, alkenyl and/or alkynyl groups containing 1 or 2 to 6 carbon atoms and/or a cycloalkyl group containing 5 or 6 ring carbon atoms, 1, 2, 3 or 4 of those carbon atoms having been replaced each independently of the others by oxygen, sulphur or nitrogen atoms.

Any arylalkyl or heteroarylalkyl group as defined herein may be substituted with one, two or more substituents, for example F, Cl, Br, I, OH, $NH_2$, SH, $N_3$, $NO_2$, alkyl groups such as methyl or ethyl, heteroalkyl groups such as methoxy, methylamino, dimethylamino or cyanide, wherein one or more, preferably one or two, of the hydrogen atoms of the arylalkyl or heteroarylalkyl residue, respectively, are independently of each other replaced by one or more of the above defined substituents.

Preferably, in the compounds of formula (I), R2 is a halogen substituted heteroaryl according to the above definition. Further preferred, R2 is a pyridyl, imidazolyl, pyrazolyl, quinolinyl, indolyl, benzimidazolyl, benzoxazolyl, benzisoxazolyl, benzthiazolyl, isoquinolinyl, pyrrolyl, oxazolyl, isoxazolyl, thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl and pyridazinyl group, wherein one or more, preferably one or two, of the hydrogen atoms of the heteroaryl group are independently of each other replaced by one or more halogen atom, preferably a chlorine or fluorine atom. Further preferred, R2 is an halogen substituted heteroaryl selected from the group consisting of 1H-indolyl, benzoimidazolyl, benzothiazolyl, quinolinyl, thiophenyl, imidazolyl, thiazolyl, pyridyl, pyrimidyl, and pyrazinyl, wherein one or more, preferably one or two, of the hydrogen atoms of the heteroaryl group are independently of each other replaced by one or more halogen atom, preferably a chlorine or fluorine atom. Especially preferred, R2 is selected from a group consisting of 5-chloro-thiophen-2-yl, 5-chloro-pyridin-2-yl, 5-chloro-1H-indol-3-yl, 6-chloro-1H-indol-3-yl, and 6-fluoro-1H-indol-3-yl.

A preferred embodiment of the present invention relates to compounds of formula (I), wherein R1 is selected from substituted or unsubstituted morpholinyl, pyrrolidinyl and piperazinyl, —O(X1) or —NX1(X2), with X1 and X2 independently selected from H, alkyl, cycloalkyl, heteroalkyl, aryl, heteroaryl, arylalkyl or heteroarylalkyl, and R2 is selected from halogen substituted heteroaryl, and R3 is selected from aryl, heteroaryl, substituted and unsubstituted 1H-indol-3-yl, substituted and unsubstituted naphthal-2-yl, substituted and unsubstituted quinolin-3-yl, phenyl, substituted phenyl, 3- or 4-fluorophenyl, 3- or 4-chlorophenyl, 3- or 4-bromophenyl, 3- or 4-iodophenyl and wherein R4 is selected from —H, —F, —Cl, —Br, —I, —NO2, hydroxy, lower alkyl, lower alkenyl or lower alkinyl, lower alkoxy, such as —$OCH_3$, —$CH_2OCH_3$ and —$CH_2OCH_2CH_3$, —NY1(Y1), with Y1 and Y2 independently selected from H, lower alkyl, lower alkoxy alkyl, hetero alkyl, aryl or heteroaryl.

A further preferred embodiment of the present invention relates to compounds of formula (I), wherein R2 is selected from halogen substituted heteroaryl, wherein the heteroaryl is selected from 1H-indolyl, benzoimidazolyl, benzothiazolyl, quinolinyl, thiophenyl, imidazolyl, thioazolyl, pyridyl, pyrimidinyl, and pyrazinyl, wherein one or more, preferably one, two or three, of the hydrogen atoms on the heteroaryl moiety are independently of each other substituted by a halogen atom, preferably by a chlorine or fluorine atom.

A further preferred embodiment of the present invention relates to compounds of formula (I), wherein R1 is selected from dimethylaminyl, diethylaminyl, 2-dimethylamino-ethylaminyl, morpholinyl, piperazinyl, N-methyl-piperazinyl, N-acetyl-piperazinyl, N-2-hydroxyethyl-piperazinyl, 2-oxo-N-alkyl-piperazinyl, 2-oxo-N-heteroalkyl-piperazinyl, pyrrolidinyl, 2-oxo-pyrrolidinyl or 2-carboxy-pyrrolidinyl.

A further preferred embodiment of the present invention relates to compounds of formula (I), wherein R1 is selected from —OX1 or —NH(X2), wherein X1 is selected from —H or lower alkyl, and X2 is selected from H, —CH$_2$CH$_2$OH, —CH$_2$CH$_2$OCH$_3$, lower alkyl, lower heteroalkyl, cycloalkyl, heteroalkyl, aryl, heteroarylalkyl, aryl or heteroarylalkyl, and R2 is selected from 5- or 6-halogen substituted 1H-indol-3-yl, 5- or 6-halogen substituted benzimidazo-3-yl, 5- or 6-halogen substituted benzimidazo-2-yl, 5-halogen substituted 2-pyridyl, 5-halogen substituted thiophen-2-yl, 4-halogen substituted imidazo-2-yl, and R3 is selected from substituted and unsubstituted 3- or 4-fluorobenzyl, 3- or 4-chlorobenzyl, 3- or 4-bromobenzyl, 3- or 4-iodobenzyl, and wherein R4 is selected from —H, —F, —Cl, —Br, —I, —NO2, hydroxy, lower alkyl, lower alkenyl or lower alkinyl, lower alkoxy, such as —OCH$_3$, —CH$_2$OCH$_3$ and —CH$_2$OCH$_2$CH$_3$, —NY1(Y1), with Y1 and Y2 independently selected from H, lower alkyl, lower alkoxy alkyl, hetero alkyl, aryl or heteroaryl.

A further preferred embodiment of the invention relates to a compound of formula (I), which is selected from the group of: 2-(4-Chloro-benzyl)-3-(5-chloro-thiophen-2-yl)-1-oxo-1,2,3,4-tetrahydro-isoquinoline-4-carboxylic acid, 2-(4-Chloro-benzyl)-3-(6-chloro-1H-indol-3-yl)-1-oxo-1,2,3,4-tetrahydro-isoquinoline-4-carboxylic acid, 2-(4-Chloro-benzyl)-3-(5-chloro-pyridin-2-yl)-1-oxo-1,2,3,4-tetrahydro-isoquinoline-4-carboxylic acid, 2-(4-Chloro-benzyl)-3-(5-chloro-1H-indol-3-yl)-1-oxo-1,2,3,4-tetrahydro-isoquinoline-4-carboxylic acid, 2-(4-Chloro-benzyl)-3-(6-fluoro-1H-indol-3-yl)-1-oxo-1,2,3,4-tetrahydro-isoquinoline-4-carboxylic acid, 3-(6-Chloro-1H-indol-3-yl)-2-[(4-chloro-phenyl)-methoxycarbonyl-methyl]-1-oxo-1,2,3,4-tetrahydro-isoquinoline-4-carboxylic acid, 2-(4-Chloro-benzyl)-3-(5-chloro-thiophen-2-yl)-1-oxo-1,2,3,4-tetrahydro-isoquinoline-4-carboxylic acid (2-methoxy-ethyl)-amide, (2-{[2-(4-chloro-benzyl)-3-(5-chloro-thiophen-2-yl)-1-oxo-1,2,3,4-tetrahydro-isoquinoline-4-carbonyl]-amino}-ethyl)-dimethyl-ammonium salt, 2-(4-Chloro-benzyl)-3-(5-chloro-pyridin-2-yl)-1-oxo-1,2,3,4-tetrahydro-isoquinoline-4-carboxylic acid (2-methoxy-ethyl)-amide, 2-(4-Chloro-benzyl)-3-(5-chloro-1H-indol-3-yl)-1-oxo-1,2,3,4-tetrahydro-isoquinoline-4-carboxylic acid (2-methoxy-ethyl)-amide, 2-(4-Chloro-benzyl)-3-(6-chloro-1H-indol-3-yl)-1-oxo-1,2,3,4-tetrahydro-isoquinoline-4-carboxylic acid (2-methoxy-ethyl)-amide, 2-(4-Chloro-benzyl)-3-(6-fluoro-1H-indol-3-yl)-1-oxo-1,2,3,4-tetrahydro-isoquinoline-4-carboxylic acid (2-methoxy-ethyl)-amide, [3-(6-Chloro-1H-indol-3-yl)-4-(2-methoxy-ethylcarbamoyl)-1-oxo-3,4-dihydro-1H-isoquinolin-2-yl]-(4-chloro-phenyl)-acetic acid ester, [3-(6-Chloro-1H-indol-3-yl)-4-(2-methoxy-ethylcarbamoyl)-1-oxo-3,4-dihydro-1H-isoquinolin-2-yl]-(4-chloro-phenyl)-acetic acid.

The compounds of formula (I) contain asymmetric C-atoms and may be present either as achiral compounds, mixtures of diastereomers, mixtures of enantiomers or as optically pure compounds.

It should be appreciated that certain compounds of formula (I) may have tautomeric forms from which only one might be specifically mentioned or depicted in the following description, different geometrical isomers (which are usually denoted as cis/trans isomers or more generally as (E) and (Z) isomers) or different optical isomers as a result of one or more chiral carbon atoms (which are usually nomenclatured under the Cahn-Ingold-Prelog or R/S system). All these tautomeric forms, geometrical or optical isomers (as well as racemates and diastereomers) and polymorphous forms are included in the invention.

A further preferred embodiment of the present invention relates to compounds of formula (I), wherein the 3,4-trans diastereomer is selected, especially preferred are the (3R,4R) enantiomerically pure compounds of formula (I).

Examples of pharmacologically acceptable salts of sufficiently basic compounds of formula (I) are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, sufficiently acidic compounds of formula (I) may form alkali or earth alkaline metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts; all of which are also further examples of salts of compounds of formula (I). Compounds of formula (I) can be solvated, especially hydrated. The hydratization can occur during the process of production or as a consequence of the hygroscopic nature of the initially water free compounds of formula (I).

The present invention also relates to pro-drugs which are composed of a compound of formula (I) and at least one pharmacologically acceptable protective group which will be cleaved off under physiological conditions, such as an alkoxy-, arylalkyloxy-, acyl-, acyloxymethyl group (e.g. pivaloyloxymethyl), an 2-alkyl-, 2-aryl- or 2-arylalkyl-oxycarbonyl-2-alkylidene ethyl group or an acyloxy group as defined herein, e.g. ethoxy, benzyloxy, acetyl or acetyloxy or, especially for a compound of formula (I), for hydroxy group (ROH), a sulfate, a phosphate (ROPO$_3$ or ROCH$_2$OPO$_3$) or an ester of an amino acid. Especially preferred are pro-drugs of the hydroxy group of a compound of I wherein R1 is H.

The present invention further provides pharmaceutical compositions comprising a compound of formula (I) as defined herein or a pharmaceutically acceptable ester, pro-drug, hydrate, solvate or salt thereof, optionally in combination with a pharmaceutically acceptable carrier.

A further preferred embodiment of the present invention relates to pharmaceutical compositions comprising a compound of formula (I) as defined herein or a pharmaceutically acceptable ester, prodrug, hydrate, solvate or salt thereof, optionally in combination with a pharmaceutically acceptable carrier, further comprising one or more other anti-tumor agents.

A further preferred embodiment of the present invention relates to pharmaceutical compositions comprising a compound of formula (I) as defined herein or a pharmaceutically acceptable ester, prodrug, hydrate, solvate or salt thereof, optionally in combination with a pharmaceutically acceptable carrier, further comprising one or more other anti-tumor agents, wherein the anti-tumor agent is selected from 16-Aza-epothilone B, Aldesleukin, Amifostine, Aranose, Bevacizumab, Bleocin, Bleomycin, BMS-184476, Bortezomib, Calcitriol, Carmustine, Canertinib, Canfosfamide, Capecitabine, Carboplatin, Carmustine, Cefixime, Ceftriaxone, Celecoxib, Celmoleukin, Cetuximab, Ciclosporin, Cisplatin, Clodronate, Cyclophosphamide, Cytarabine, Deoxorubicin, Desoxyepothilone B, Diethylstilbestrol, Diflomotecan, Docetaxel, Doxorubicin, Edatrexate, Efaproxiral, EKB-569, Epirubicin, Epratuzumab, Erlotinib, Etoposide, ET-18-OCH3, Exatecan, Fludarabine, Fluorouracil, Folinic acid, Galarubicin, Gefinitib, Gemcitabine, Gemtuzumab, Gimatecan, Glufosfamide, Granisetron, Homoharringtonine, Hyaluronic acid, Ibandronate, Ibritumomab, Ifosfamide, Imatinib, Interferon alfa, Interferon alfa-2a, Interferon alfa-2b, Irinotecan, Isoflavone, Isotretinoin, Ixabepilone, Ketoconazole, Lapatinib, Leflunomide, Lenograstim, Leucovorin, Lexidronam, Linezolid, Lometrexol, Lurtotecan, MEN10755, Methotrexate, Mitomycin, Neridronate, Nimesulide, Nitroglycerin, 06-Benzylguanine, Omeprazole, Ortataxel, Oxaliplatin, Paclitaxel, Patupilone, Pegfilgrastim, PEG-filgrastim, Pelitinib, Pemetrexed, Pentostatin, Perifosine, Plevitrexed, Polyprenoic acid, Quinupristin, Raloxifene, Raltitrexed, Ramosetron, Retinoic acid, Risedroante, Rituximab, Rofecoxib, Rubitecan, S-9788, Sabarubicin, Sargramostim, Satraplatin, SN-38, Sorafenib, Suberanilohydroxamic acid, Sutent, Tamoxifen, Taxotere, Tazarotene, Tegafur, Temozolamide, Tesmilifene, Tetrodotoxin, Thalidomide, Tipifarnib, Topotecan, Trabectedin, Trastuzumab, Traszutumab, Tretinoin, Vatalanib, Vincristine, Vinorelbine, Vinscristine, ZD-6474, Zoledronate or Zosuquidar.

A further preferred embodiment of the present invention relates to pharmaceutical compositions comprising a compound of formula (I) as defined herein or a pharmaceutically acceptable ester, prodrug, hydrate, solvate or salt thereof, optionally in combination with a pharmaceutically acceptable carrier, further comprising one or more antiviral agents, wherein the antiviral agent is selected from 3TC, Abacavir, Adefovir dipivoxil, Acyclovir, Amprenavir, Amantadine, Amoxovir, AZT, Clevudine, Delavirdine, d4T, Emtricitabine, Entecavir, Famciclovir, Ganciclovir, Indinavir, Lamivudine, Nelfinavir, Nevirapine, Oseltamavir, Rimantadine, Ritonavir, Saquinavir, Septrin, Telbivudine, Tenofovir, Valacyclovir, Valtorcitabine, Valopicitabine or Zanamivir.

It is a further object of the present invention to provide a compound of formula (I) as defined herein or a pharmaceutical composition as defined herein for the preparation of a medicament for the treatment of cancer.

A compound selected from formula (I) of the present invention is a HDM2 ligand and shows binding affinities from about 1 nM to about 100 µM to HDM2, preventing binding of p53 and other proteins, inhibition of proliferation and induction of apoptosis in cell based assays.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolongs the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound being administered, the route of administration, the condition being treated, as well as the patient being treated.

As mentioned above, therapeutically useful agents that contain compounds of formula (I), their solvates, salts or formulations are also comprised in the scope of the present invention. In general, compounds of formula (I) will be administered by using the known and acceptable modes known in the art, either alone or in combination with any other therapeutic agent.

For oral administration such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdermal, for example via an transdermal delivery system (TDS) such as a plaster containing the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatine, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, polyols. For the production of liquid solutions, emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilization, e.g. UV stabilizers, emulsifiers, sweetener, aromatizers, salts to change the osmotic pressure, buffers, coating additives and antioxidants.

In general, in the case of oral or parenteral administration to adult humans weighing approximately 80 kg, a daily dosage of about 10 mg to about 10,000 mg, preferably from about 20 mg to about 1,000 mg, should be appropriate, although the upper limit may be exceeded when indicated. The daily dosage can be administered as a single dose or in divided doses, or for parenteral administration, it may be given as continuous infusion or subcutaneous injection.

The compounds of the present invention can be prepared according to the following procedure:

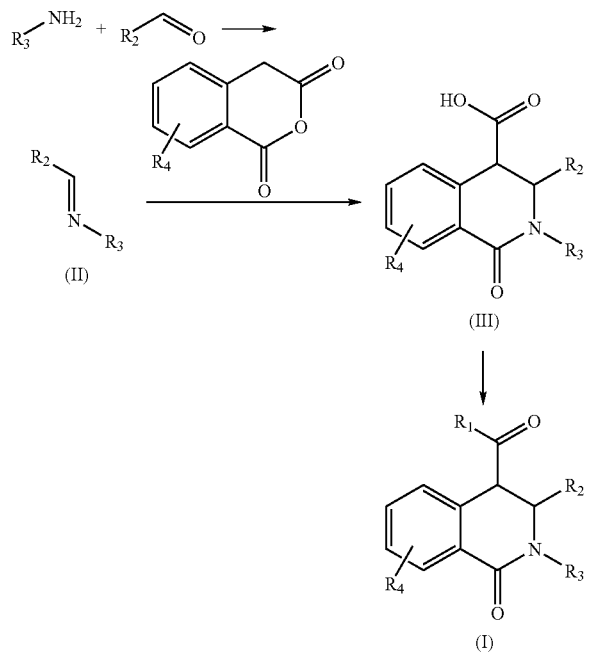

An amine and an aldehyde are reacted to give an azomethine of the formula (II), this azomethine is reacted with an homophthalic acid anhydride derivative, giving compounds of formula (III), which are than converted to esters, amides or left unchanged to give compounds of formula (I). These compounds of formula (I) can be further derivatized such as making esters or salts from acids, salts from amines or cleaving protecting groups found in substituents R1 to R4.

The present invention encompasses the following Examples:

EXAMPLE 1

General Procedure for the Synthesis of 1-oxo-1,2,3,4-tetrahydro-isoquinoline-4-carboxylic acids Equimolar amounts of an aldehyde and a primary amine are added at room temperature in a solvent like dichloromethane, tetrahydrofurane, chloroforme, methanol or ethanol to form the corresponding azomethine. A dehydrating agent like a mol sieve can be added to facilitate the reaction. After a time period of 1 hour up to 1 day of reaction, equimolar amounts of a homophthalic acid anhydride derivative is added and the reaction mixture is refluxed. Catalytic amounts of boron trifluoride etherate can be added in catalytic or equimolar amounts as a catalyst to facilitate product formation. After a time period of 1 hour up to 1 day of reaction the reaction mixture is cooled down. The resulting 1-oxo-1,2,3,4-tetrahydro-isoquinoline-4-carboxylic acid derivative is filtered off and washed with dichloromethane, hexane and ethylacetate if it has precipitated out. If the product does not precipitate, from the reaction mixture the solvent is evaporated in vacuum, the product is re-crystallized from ethanol or purified via standard column chromatographic methods. This crystalline product may be a diastereomeric mixture of the 3,4-trans isomers.

Complete Isomerization to the Trans-Isomer:

The crude reaction mixture of cis and trans isomers is refluxed for 2 hours (5 mL/mmol) in acetic acid. After cooling the mixture to room temperature, ether (2.5 mL/mmol) and water (2.5 mL/mmol) are added. The reaction mixture is stirred for 12 hours. The resulting white precipitate is filtered off and washed with cold ether.

EXAMPLE 2

According to the general procedure in example 1, the following compounds were prepared:

2.a 2-(4-Chloro-benzyl)-3-(5-chloro-thiophen-2-yl)-1-oxo-1,2,3,4-tetrahydro-isoquinoline-4-carboxylic acid. Molecular Weight=432.3286, calculated from Molecular Formula=C21H15Cl2NO3S. $(M+H)^+$ observed 432.2. 1H-NMR (DMSO-D6, ppm)=4.15 (1H, d, J=14.8 Hz), 4.22 (1H, s), 5.04 (1H, d, J=14.8 Hz), 5.48 (1H, s).

2.b 2-(4-Chloro-benzyl)-3-(6-chloro-1H-indol-3-yl)-1-oxo-1,2,3,4-tetrahydro-isoquinoline-4-carboxylic acid. Molecular Weight=465.3398, calculated from Molecular Formula=C25H18Cl2N2O3. $(M+H)^+$ observed 465.2.

2.c 2-(4-Chloro-benzyl)-3-(5-chloro-pyridin-2-yl)-1-oxo-1,2,3,4-tetrahydro-isoquinoline-4-carboxylic acid. Molecular Weight=427.2904, calculated from Molecular Formula=C22H16Cl2N2O3. $(M+H)^+$ observed 427.4.

2.d 2-(4-Chloro-benzyl)-3-(5-chloro-1H-indol-3-yl)-1-oxo-1,2,3,4-tetrahydro-isoquinoline-4-carboxylic acid. Molecular Weight=465.3398, calculated from Molecular Formula=C25H18Cl2N2O3. $(M+H)^+$ observed 465.3.

2.e 2-(4-Chloro-benzyl)-3-(6-fluoro-1H-indol-3-yl)-1-oxo-1,2,3,4-tetrahydro-isoquinoline-4-carboxylic acid. Molecular Weight=448.8852, calculated from Molecular Formula=C25H18ClFN2O3. $(M+H)^+$ observed 448.9.

2.f 3-(6-Chloro-1H-indol-3-yl)-2-[(4-chloro-phenyl)-methoxycarbonyl-methyl]-1-oxo-1,2,3,4-tetrahydro-isoquinoline-4-carboxylic acid. Molecular Weight=523.3769, calculated from Molecular Formula=C27H20Cl2N2O5. $(M+H)^+$ observed 523.6.

EXAMPLE 3

General Procedure for the Synthesis of the 1-oxo-1,2,3,4-tetrahydro-isoquinoline-4-carboxamides The corresponding carboxylic acid from example 1 (1 mmol) is dissolved in DMF (2 mL/mmol) and EDCI or an equivalent coupling reagent such as EDCI (2 mmol) is added. The reaction mixture is stirred for 5 min up to 1 hour until a clear solution is obtained. Then, the corresponding amine (2 mmol) is added and the mixture is stirred for 12 or up to 48 hours, first at room temperature than at 50° C. The reaction mixture is diluted with dichloromethane and washed with brine two times. The organic phase is then dried over magnesium sulphate and evaporated. The desired product is purified by column chromatography on silica gel with the elution system ethyl acetate-hexane or with the system acetonitrile/water 60/40. Compound 2 is obtained as a brown solid (12 mg) with high purity (>95%). Alternatively, the final product is purified either by re-crystallization from ethanol or ether.

EXAMPLE 4

According to the general procedure in example 3, the following compounds were prepared:

4.a 2-(4-Chloro-benzyl)-3-(5-chloro-thiophen-2-yl)-1-oxo-1,2,3,4-tetrahydro-isoquinoline-4-carboxylic acid (2-methoxy-ethyl)-amide. Molecular Weight=489.4245, calculated from Molecular Formula=C24H22Cl2N2O3S. (M+H)$^+$ observed 488.6. 1H-NMR (DMSO-D6, ppm)=3.16 (3H, s, OCH3), 3.79 (1H, s), 4.04 (1H, d, J=14.7 Hz), 5.23 (1H, d, J=14.7 Hz), 5.52 (1H, s), 8.24 (1H, s, NH).

4.b (2-{[2-(4-chloro-benzyl)-3-(5-chloro-thiophen-2-yl)-1-oxo-1,2,3,4-tetrahydro-isoquinoline-4-carbonyl]-amino}-ethyl)-dimethyl-ammonium formate. Molecular Weight=503.4749+45.0179, calculated from Molecular Formula=C25H26Cl2N3O2S.CHO2. (M)$^+$ observed 502.7. 1H-NMR (DMSO-D6, ppm)=2.55 (3H, s, OCH3), 3.85 (1H, s), 3.88 (1H, d, J=14.1 Hz), 5.32 (1H, d, J=14.1 Hz), 5.41 (1H, s), 8.23 (1H, s, NH).

4.c 2-(4-Chloro-benzyl)-3-(5-chloro-pyridin-2-yl)-1-oxo-1,2,3,4-tetrahydro-isoquinoline-4-carboxylic acid (2-methoxy-ethyl)-amide. Molecular Weight=484.3864, calculated from Molecular Formula=C25H23Cl2N3O3. (M+H)$^+$ observed 483.4. 1H-NMR (DMSO-D6, ppm)=3.18 (3H, s, OCH3), 4.13 (1H, d, J=14.4 Hz), 4.20 (1H, s), 5.30 (1H, d, J=14.4 Hz), 5.51 (1H, s), 8.45 (1H, s, NH).

4.d 2-(4-Chloro-benzyl)-3-(5-chloro-1H-indol-3-yl)-1-oxo-1,2,3,4-tetrahydro-isoquinoline-4-carboxylic acid (2-methoxy-ethyl)-amide. Molecular Weight=522.4358, calculated from Molecular Formula=C28H25Cl2N3O3. (M+H)$^+$ observed 523.5.

4.e 2-(4-Chloro-benzyl)-3-(6-chloro-1H-indol-3-yl)-1-oxo-1,2,3,4-tetrahydro-isoquinoline-4-carboxylic acid (2-methoxy-ethyl)-amide. Molecular Weight=522.4358, calculated from Molecular Formula=C28H25Cl2N3O3. (M+H)$^+$ observed 522. 1H-NMR (DMSO-D6, ppm)=2.81 (3H, s, OCH3), 3.96 (1H, d, J=15.2 Hz), 4.07 (1H, s), 5.28 (1H, d, J=15.2 Hz), 5.39 (1H, s), 8.10 (1H, s, NH), 10.50 (1H, s, NH).

4.f 2-(4-Chloro-benzyl)-3-(6-fluoro-1H-indol-3-yl)-1-oxo-1,2,3,4-tetrahydro-isoquinoline-4-carboxylic acid (2-methoxy-ethyl)-amide. Molecular Weight=505.9812, calculated from Molecular Formula=C28H25ClFN3O3. (M+H)$^+$ observed 506. 1H-NMR (DMSO-D6, ppm)=3.18 (3H, s, OCH3), 3.94 (1H, d, J=15.2 Hz), 4.05 (1H, s), 5.31 (1H, d, J=15.2 Hz), 5.51 (1H, s), 8.12 (1H, s, NH), 9.21 (1H, s, NH).

4.g [3-(6-Chloro-1H-indol-3-yl)-4-(2-methoxy-ethylcarbamoyl)-1-oxo-3,4-dihydro-1H-isoquinolin-2-yl]-(4-chloro-phenyl)-acetic acid methyl ester. Molecular Weight=580.4728, calculated from Molecular Formula=C30H27Cl2N3O5. (M+H)$^+$ observed 580.3.

EXAMPLE 5

Using [3-(6-Chloro-1H-indol-3-yl)-4-(2-methoxy-ethylcarbamoyl)-1-oxo-3,4-dihydro-1H-isoquinolin-2-yl]-(4-chloro-phenyl)-acetic acid methyl ester from Example 4.f the acid [3-(6-Chloro-1H-indol-3-yl)-4-(2-methoxy-ethylcarbamoyl)-1-oxo-3,4-dihydro-1H-isoquinolin-2-yl]-(4-chloro-phenyl)-acetic acid was prepared by treatment with lithium hydroxide in tetrahydrofurane. Molecular Weight=566.4457, calculated from Molecular Formula=C29H25Cl2N3O5. (M$^+$) observed 566.2.

EXAMPLE 5

Proliferation Assay:

5000 cells were plated in each well of 96-well flat bottom plates, and incubated overnight at 37° C. in 5% CO$_2$. The growth of plated cells was measured by adding 7.5 µM of WST-1 reagent (Roche Applied Sciences, Germany) to 3 control wells and measuring OD$_{650}$ and OD$_{450}$ absorbances with a SpectraMax250 plate reader. If the OD$_{650}$-OD$_{450}$ values were above 0.5, the remainder of the plate was used for incubation with MCP compounds, other pharmacological agents or solvent control for 48 hours. After this incubation, WST-1 reagent was added to the wells and OD$_{650}$-OD$_{450}$ values were calculated as before. Triplicate wells were assayed for each conditions and standard deviation was determined: all experiments were performed at least three times independently.

EXAMPLE 6

Apoptosis Annexin V and Tunel Assay:

Annexin V and BrdU-incorporation levels were determined with Guava Nexin and Guava Tunel kits using a Guava Personal Cell Analysis System (PCAS, Guava Technologies, Hayward, Calif.) according to the manufacturer's instruction. 1×10$^6$ PA-1 and PA-1/E6 cells were cultured in BME media supplemented with 10% FBS and various concentrations of NXN523, NXN527 or DMSO for 24 h. Nutlin-3, Racemic (Calbiochem, Roche) at 10 µM was applied as positive control. For Guava Nexin assay cells were trypsinized and collected by centrifuging at 1000 rpm for 5 min at 4° C. After washing with ice-cold 1× Nexin buffer, cells were resuspended in the same buffer, labeled with Annexin V-PE and 7-aminoactinomycin D in the dark on ice for 20 min, and then analyzed with the PCAS. According to the manufacturer protocol for Guava Tunel assay cells were resuspended in 1% paraformaldehyde, incubated on ice for 60 min, washed in ice-cold PBS buffer. Than cells were fixed in ice-cold 70% ethanol for at least 16 h at −20° C. After incubation cells were labeled with BrdU DNA labeling mix for 60 min at 37° C., collected by centrifugation at 1000 rpm for 5 min. Cells were resuspended in anti-BrdU staining mix and incubated at room temperature for 45 min in the dark, and then analyzed with the PCAS.

EXAMPLE 7

Apoptosis Assays and siRNA Studies:

Temperature-sensitive H1299 clones were seeded onto 6-well plates at a density of 50,000 cells/well. Saos2 cells were plated at 1×106 cells/100-mm plate. Cells were shifted to 32° C. and harvested at the times indicated after temperature shift. Control cells were maintained at 39° C. TUNEL and multi-caspase assays were conducted using the Guava Personal Cytometer (Guava Technologies) using the Guava TUNEL and multi-caspase detection kits, using protocols provided by the manufacturer (Guava Technologies). For the siRNA studies, an equal number of H1299 cells with temperature-sensitive wt p53 were seeded onto a 10-cm plate; after 24 h, 25 µl of siRNA for PUMA (20 µM BBC3 SmartPool oligonucleotides; Dharmacon) or control RNA (20 µM, Dharmacon) were transfected using Oligofectamine as per the manufacturer (Invitrogen). After 24 h of temperature shift, cells were harvested and subjected to Western analysis as described above.

The invention claimed is:

1. A compound of general formula (A) and pharmaceutically acceptable salt or an ester thereof,

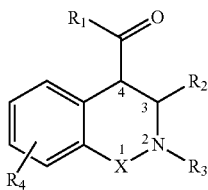

formula (A)

wherein X is C=O,

R¹ is selected from substituted or unsubstituted morpholinyl, substituted or unsubstituted pyrrolidinyl and substituted or unsubstituted piperazinyl, —NX₁(X₂), with X₁ and X₂ independently selected from H, alkyl, cycloalkyl, heteroalkyl, aryl, heteroaryl, arylalkyl or heteroarylalkyl, wherein R₂ is a heteroaryl, selected from the group of pyridyl, imidazolyl, pyrazolyl, quinolinyl, indolyl, benzoimidazolyl, benzoxazoyl, benzisoazoyl, benzthiazolyl, isoquinolinyl, pyrrolyl oxazolyl, isoxazolyl, thiazolyl, isothiazolyl, 1,2,3-triazolyl, 1,2,4-triazolyl, oxadiazolyl, thiadiazolyl, thiophenyl, indazolyl, tetrazolyl, pyrazinyl, primidinyl and pyridazinyl groups said heteroaryl being optionally substituted with at least one substituent independently selected from the group of F, Cl, Br, I, OH, NH₂, SH, N₃, NO2, alkyl, heteroalkyl, methylamino, dimethylamino or cyanide, wherein R₃ is selected from aryl, heteroaryl, arylalkyl or heteroarylalkyl, wherein R₄ is selected from —H, —F, —Cl, —Br, —I, —NO₂, hydroxy, lower alkyl, lower alkenyl or lower alkinyl, lower alkoxy, —CH₂OCH₃ and —CH₂OCH₂CH₃, —NY₁(Y₂), with Y₁ and Y₂ independently selected from H, lower alkyl, lower alkoxy alkyl, hetero alkyl, aryl or heteroaryl.

2. The compound according to claim 1, wherein R₂ is a halogen substituted heteroaryl.

3. The compound according to claim 2, wherein R₂ is selected from the group consisting of 1H-indolyl, benzoimidazolyl, benzothiazolyl, quinolinyl, thiophenyl, imidazolyl, thioazolyl, pyridyl, pyrimidinyl, and pyrazinyl.

4. The compound according to claim 1, wherein R₃ is an aryl or heteroaryl, selected from the group consisting of substituted and unsubstituted 1H-indol-3-yl, substituted and unsubstituted naphthal-2-yl, substituted and unsubstituted quinolin-3-yl, phenyl, substituted phenyl.

5. The compound according to claim 1, wherein R₃ is a substituted aralkyl selected from the group consisting of 3- or 4-fluorobenzyl, 3- or 4-chlorobenzyl, 3- or 4-bromobenzyl, 3- or 4-iodobenzyl.

6. The compound according to claim 1, wherein R₁ is —NH(X₂), wherein X₁ is selected from —H or lower alkyl, and X₂ is selected from H, —CH₂CH₂OH, —CH₂CH₂OCH₃, lower alkyl, lower heteroalkyl, cycloalkyl, heteroalkyl, aryl, heteroarylalkyl, aryl or heteroarylalkyl.

7. The compound according to claim 1, wherein R₁ is selected from dimethylaminyl, diethylaminyl, 2-dimethylaminoethylaminyl, morpholinyl, piperazinyl, N-methyl-piperazinyl, N-acetyl-piperazinyl, N-2-hydroxyethyl-piperazinyl, 2-oxo-N-alkyl-piperazinyl, 2-oxo-N-heteroalkyl-piperazinyl, pyrrolidinyl, 2-oxo-pyrrolidinyl or 2-carboxy-pyrrolidinyl.

8. The compound according to claim 1, selected from the group consisting of: 2-(4-Chloro-benzyl)-3-(5-chloro-thiophen-2-yl)-1-oxo-1,2,3,4-tetrahydro-isoquinoline-4-carboxylic acid (2-methoxy-ethyl)-amide, (2-{[2-(4-chloro-benzyl)-3-(5-chloro-thiophen-2-yl)-1-oxo-1,2,3,4-tetrahydro-isoquinoline-4-carbonyl]-amino}-ethyl)-dimethyl-ammonium salt, 2-(4-Chloro-benzyl)-3-(5-chloro-pyridin-2-yl)-1-oxo-1,2,3,4-tetrahydro-isoquinoline-4-carboxylic acid (2-methoxy-ethyl)-amide, 2-(4-Chloro-benzyl)-3-(5-chloro-1H-indol-3-yl)-1-oxo-1,2,3,4-tetrahydro-isoquinoline-4-carboxylic acid (2-methoxy-ethyl)-amide, 2-(4-Chloro-benzyl)-3-(6-chloro-1H-indol-3-yl)-1-oxo-1,2,3,4-tetrahydro-isoquinoline-4-carboxylic acid (2-methoxy-ethyl)-amide, 2-(4-Chloro-benzyl)-3-(6-fluoro-1H-indol-3-yl)-1-oxo-1,2,3,4-tetrahydro-isoquinoline-4-carboxylic acid (2-methoxy-ethyl)-amide, [3-(6-Chloro-1H-indol-3-yl)-4-(2-methoxy-ethylcarbamoyl)-1-oxo-3,4-dihydro-1H-isoquinolin-2-yl]-(4-chloro-phenyl)-acetic acid ester, [3-(6-Chloro-1H-indol-3-yl)-4-(2-methoxy-ethylcarbamoyl)-1-oxo-3,4-dihydro-1H-isoquinolin-2-yl]-(4-chloro-phenyl)-acetic acid.

9. The compound according to claim 4, wherein R3 is a substituted phenyl selected from the group consisting of 3- or 4-fluorophenyl, 3- or 4-chlorophenyl, 3- or 4-bromophenyl, 3- or 4-iodophenyl.

10. A pharmaceutical composition comprising a compound according to claim 1 or a pharmaceutically acceptable ester, hydrate, or salt thereof, in combination with a pharmaceutically acceptable carrier.

11. A pharmaceutical composition according to claim 10 comprising one or more other anti-tumor agents.

12. A pharmaceutical composition according to claim 11, wherein the anti-tumor agent is selected from 16-Aza-epothilone B, Aldesleukin, Amifostine, Aranose, Bevacizumab, Bleocin, Bleomycin, BMS-184476, Bortezomib, Calcitriol, Carmustine, Canertinib, Canfosfamide, Capecitabine, Carboplatin, Carmustine, Cefixime, Ceftriaxone, Celecoxib, Celmoleukin, Cetuximab, Ciclosporin, Cisplatin, Clodronate, Cyclophosphamide, Cytarabine, Deoxorubicin, Desoxyepothilone B, Diethylstilbestrol, Diflomotecan, Docetaxel, Doxorubicin, Edatrexate, Efaproxiral, EKB-569, Epirubicin, Epratuzumab, Erlotinib, Etoposide, ET-18-OCH3, Exatecan, Fludarabine, Fluorouracil, Folinic acid, Galarubicin, Gefinitib, Gemcitabine, Gemtuzumab, Gimatecan, Glufosfamide, Granisetron, Homoharringtonine, Hyaluronic acid, Ibandronate, Ibritumomab, Ifosfamide, Imatinib, Interferon alfa, Interferon alfa-2a, Interferon alfa-2b, Irinotecan, Isoflavone, Isotretinoin, Ixabepilone, Ketoconazole, Lapatinib, Leflunomide, Lenograstim, Leucovorin, Lexidronam, Linezolid, Lometrexol, Lurtotecan, MEN-10755, Methotrexate, Mitomycin, Neridronate, Nimesulide, Nitroglycerin, O6-Benzylguanine, Omeprazole, Ortataxel, Oxaliplatin, Paclitaxel, Patupilone, Pegfilgrastim, PEG-filgrastim, Pelitinib, Pemetrexed, Pentostatin, Perifosine, Plevitrexed, Polyprenoic acid, Quinupristin, Raloxifene, Raltitrexed, Ramosetron, Retinoic acid, Risedroante, Rituximab, Rofecoxib, Rubitecan, S-9788, Sabarubicin, Sargramostim, Satraplatin, SN-38, Sorafenib, Suberanilohydroxamic acid, Tamoxifen, Taxotere, Tazarotene, Tegafur, Temozolamide, Tesmilifene, Tetrodotoxin, Thalidomide, Tipifarnib, Topotecan, Trabectedin, Trastuzumab, Traszutumab, Tretinoin, Vatalanib, Vincristine, Vinorelbine, Vinscristine, ZD-6474, Zoledronate or Zosuquidar.

13. A pharmaceutical composition according to claim 10 comprising at least one antiviral agents.

14. A pharmaceutical composition according to claim 13, wherein the antiviral agent is selected from 3TC, Abacavir, Adefovir dipivoxil, Acyclovir, Amprenavir, Amantadine, Amoxovir, AZT, Clevudine, Delavirdine, d4T, Emtricitabine, Entecavir, Famciclovir, Ganciclovir, Indinavir, Lamivudine, Nelfinavir, Nevirapine, Oseltamavir, Rimantadine, Ritonavir, Saquinavir, Septrin, Telbivudine, Tenofovir, Valacyclovir, Valtorcitabine, Valopicitabine or Zanamivir.

* * * * *

UNITED STATES PATENT AND TRADEMARK OFFICE
CERTIFICATE OF CORRECTION

PATENT NO.        : 8,367,699 B2                                           Page 1 of 1
APPLICATION NO.   : 12/441266
DATED             : February 5, 2013
INVENTOR(S)       : Weber et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 792 days.

Signed and Sealed this
First Day of September, 2015

Michelle K. Lee
*Director of the United States Patent and Trademark Office*